(12) United States Patent
Pirovic

(10) Patent No.: US 7,095,167 B2
(45) Date of Patent: Aug. 22, 2006

(54) GERMICIDAL LOW PRESSURE MERCURY VAPOR DISCHARGE LAMP WITH AMALGAM LOCATION PERMITTING HIGH OUTPUT

(75) Inventor: Arpad Pirovic, Woodbridge, CT (US)

(73) Assignee: Light Sources, Inc., Orange, CT (US)

( * ) Notice: Subject to any disclaimer, the term of this patent is extended or adjusted under 35 U.S.C. 154(b) by 147 days.

(21) Appl. No.: 10/406,759

(22) Filed: Apr. 3, 2003

(65) Prior Publication Data

US 2004/0195954 A1 Oct. 7, 2004

(51) Int. Cl.
*H01J 17/26* (2006.01)

(52) U.S. Cl. .............. 313/490; 313/564; 313/550

(58) Field of Classification Search .......... 313/490, 313/550, 552, 564–565, 231.71; 250/436; 210/748
See application file for complete search history.

(56) References Cited

U.S. PATENT DOCUMENTS

| | | | | |
|---|---|---|---|---|
| 4,471,225 | A | * | 9/1984 | Hillman ............ 250/436 |
| 4,700,101 | A | | 10/1987 | Ellner et al. |
| 4,968,891 | A | * | 11/1990 | Jhawar et al. ........ 250/438 |
| 5,294,867 | A | | 3/1994 | Grossman |
| 5,352,359 | A | * | 10/1994 | Nagai et al. ......... 210/192 |
| 5,757,129 | A | | 5/1998 | Schafnitzel et al. |
| 6,310,437 | B1 | * | 10/2001 | Blau et al. ........... 313/552 |
| 6,337,539 | B1 | | 1/2002 | Yorifuji et al. |
| 6,404,122 | B1 | | 6/2002 | Lankhorst et al. |

FOREIGN PATENT DOCUMENTS

WO WO 96/31902 10/1996

OTHER PUBLICATIONS

IESNA Light Sources Committee, Understanding and controlling the effects of temperature on fluorescent lamp systems, 1996, pp. 1-11.

J. Bloem et al, Some new mercury alloys for use in fluorescent lamps, Apr. 1977, Journal of Illuminating Engineering Society, pp. 141-147.

* cited by examiner

*Primary Examiner*—Karabi Guharay
(74) *Attorney, Agent, or Firm*—Fattibene & Fattibene; Paul A. Fattibene; Arthur T. Fattibene

(57) ABSTRACT

A germicidal lamp having amalgam for controlling mercury vapor pressure contained in a location facilitating efficient high output operation. A low pressure mercury vapor discharge lamp has an amalgam container containing an amalgam positioned behind an electrode out of the arc path or space. The amalgam position is retained during high wall loading of the lamp preventing the amalgam from moving out of position. Efficient operation with high current loads and resulting high wall loading and temperatures is possible. The germicidal lamp is particularly suited to being positioned vertically in a waste water treatment system.

9 Claims, 3 Drawing Sheets

GERMICIDAL LOW PRESSURE MERCURY VAPOR DISCHARGE LAMP WITH AMALGAM LOCATION PERMITTING HIGH OUTPUT

FIELD OF THE INVENTION

The present invention relates generally to low pressure mercury vapor discharge germicidal lamps used to disinfect or purify fluids, and more particularly to a germicidal lamp having a structure permitting high output and relatively high temperature operation.

BACKGROUND OF THE INVENTION

Low pressure mercury vapor discharge lamps are commonly used to generate ultraviolet radiation and used to irradiate a fluid to kill potentially harmful organisms contained in the fluid. Often, relatively high doses of ultraviolet radiation are required. The necessary relatively high doses of ultraviolet radiation typically require the use of multiple germicidal lamps. The use of multiple germicidal lamps increases expenses, as well as maintenance. Therefore, it is desirable to use fewer higher output germicidal lamps. However, producing a high output germicidal lamp is not without difficulties. During operation of a low pressure mercury vapor discharge lamp, the vapor pressure of the mercury greatly affects lamp operation. A predetermined vapor pressure is desirable for efficient operation of the lamp. However, under heavy loads used to produce a high output, mercury vapor pressure may increase reducing the efficiency and operation of the lamp. Amalgam has often been used to control the mercury vapor pressure within the lamp, permitting the lamp to operate more efficiently. However, the higher temperatures occurring at high loading of the lamp often cause the amalgam to melt. If the amalgam melts, it will move out of position and could make contact with an electrode and cause possible shorting or ineffective operation of the lamp.

A germicidal lamp using an amalgam is disclosed in Patent Cooperation Treaty international application No. PCT/DE96/00647 having a publication number of WO96/31902 and published Oct. 10, 1996, entitled "Low Pressure Mercury Vapor Discharge Lamp". Therein disclosed is a low pressure mercury vapor discharge lamp having an amalgam placed along the inner wall between the electrodes. The lamp tube is in mechanical contact with a cooler on the outside of the lamp adjacent the location of the amalgam. While this lamp structure is helpful in keeping the amalgam cool and therefore permitting higher loading of the lamp to improve output, the amalgam could still melt causing the amalgam to move out of position. This is particularly problematic in applications where the lamp is held vertically rather than horizontally, which could result in the amalgam falling downward onto one of the electrodes.

Therefore, there is a need for a low pressure mercury vapor discharge germicidal lamp for producing a high output of ultraviolet radiation that reduces the possibility of an amalgam melting or moving out of a desired location during high loading.

SUMMARY OF THE INVENTION

The present invention relates to a germicidal low pressure mercury vapor discharge lamp for operating under a high load having improved operation and output. An amalgam is positioned out of the arc path during operation of the lamp. An amalgam container is positioned behind the electrode in a relatively cool location or cold spot. The amalgam container is open, permitting the surface of the amalgam to be exposed to the interior space of the lamp, yet restricted to prevent the amalgam from moving out of position from behind the electrode where it is out of the arc path.

One embodiment comprises a germicidal lamp system having a plurality of elongated lamps held vertically within a fluid. The amalgam container holds amalgam in a location behind the electrode preventing the amalgam from moving out of position during high loading of the germicidal lamps. The positioning of the amalgam in a cooler location makes possible the higher loading of the germicidal lamp.

Accordingly, it is an object of the present invention to provide a high output germicidal lamp capable of operating at high wall loads.

It is another object of the present invention to provide a germicidal lamp that is capable of using amalgams that may melt at the internal operating temperature of the germicidal lamp.

It is another object of the present invention to provide a germicidal lamp that can effectively operate over a wide temperature range.

It is an advantage of the present invention that the germicidal lamp can be held vertically during operation.

It is another advantage of the present invention that the amalgam is held in a cooler location outside of the arc path or positive column.

It is a feature of the present invention that the amalgam is held in a position behind an electrode.

It is another feature of the present invention that a container is used to prevent the amalgam from moving out of a desired position.

These and other objects, advantages, and features will become readily apparent in view of the following more detailed description.

DETAILED DESCRIPTION OF THE PREFERRED EMBODIMENTS

Figure 1:
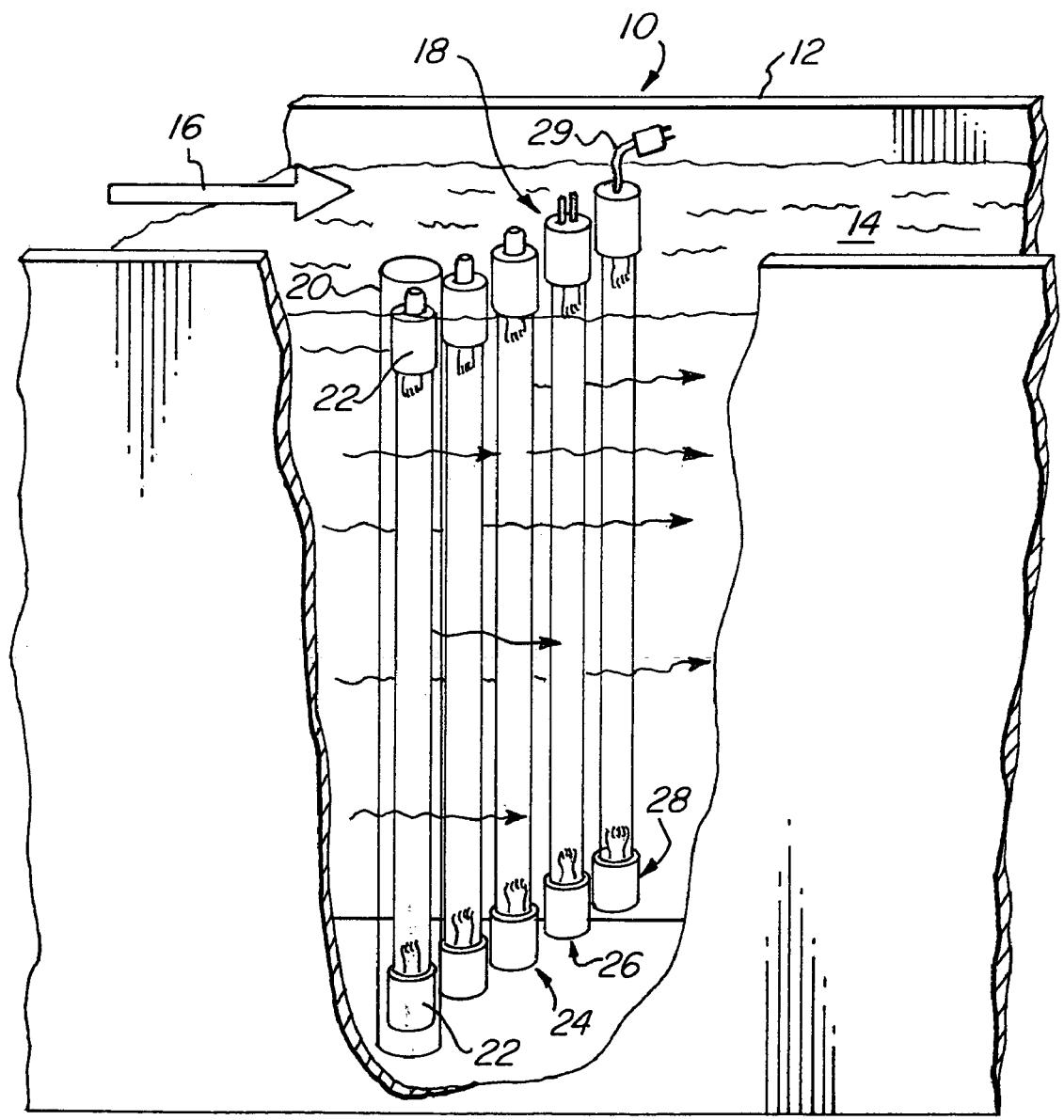
FIG. 1 schematically illustrates a plurality of germicidal lamps and a germicidal system according to the present invention.

FIG. 1 schematically illustrates a germicidal system 10 of the present invention. A container 12 holds a fluid 14 therein. The fluid may be waste water, air, or any other fluid type material that is to be purified or disinfected using ultraviolet radiation. The fluid or waste water 14 flows in the direction indicated by arrow 16. A plurality of germicidal lamps 18 are vertically placed within the fluid 14. Each of the plurality of lamps 18 may have a variety of different configurations. By way of example, several differently configured germicidal lamps are shown for illustrative purposes. Additionally, each of the germicidal lamps 18 may be placed in a protective sleeve 20. At each end of the lamp, end caps 22 are placed.

The end caps 22 may be made of a plastic material and sealed against the glass tube of the germicidal lamp. The germicidal lamp may be sealed within the protective sleeve 20 by rubber seals or any other equivalent or conventional technique. For illustration purposes, a double ended lamp 24 is shown. The double ended lamp 24 has electrical connections or pins at either end of the lamp. A single ended lamp 26 may also be used. The single ended lamp 26 has two pins on one end for connecting to an electrical power source with a conductive wire extending along the length of the lamp to form an electrical connection with an electrode at the opposite end of the germicidal lamp. Such a single ended lamp 26 is more fully disclosed in U.S. Pat. No. 4,700,101 entitled "Elongated Tubular Lamp Construction" and issuing to Ellner et al on Oct. 13, 1987, which is herein incorporated by reference. The germicidal lamp may also be a single ended pigtail type lamp 28. The single ended pigtail lamp 28 has a pigtail 29 attached to the electrical terminals of the electrodes to facilitate an electrical connection. The pigtail 29 comprises flexible wires electrically attached or coupled to the electrodes and a connector having pins for connecting to a power source. Any conventional or equivalent electrical connection may be made with different types of germicidal lamps, as is well known.

In a germicidal lamp held vertically within a fluid column, it is often desirable to operate the germicidal lamp at high wall loading to improve output. The high wall loading may be greater than 250 milliwatts per centimeter squared. Comparatively, a conventional fluorescent lamp is generally only operated at a wall load of about 100 milliwatts per centimeter squared. During high current operation, with the resulting high wall load, the internal temperature of the lamp may increase to greater than 140° centigrade. At these temperatures, the mercury vapor pressure within the germicidal lamp increases to unacceptable levels. In order to keep the mercury vapor pressure within predetermined limits for effective operation of the lamps, amalgams are used to absorb and release mercury as required to maintain efficient operation. However, at high temperatures, the amalgam may melt, limiting their effectiveness and causing them to move out of position within the germicidal lamp. The present invention positions the amalgam outside of the arc path or outside of the positive column at a location behind the electrode in a cooler spot. The amalgam is positioned at a location where the internal temperature or wall temperature of the germicidal lamp is less than about 140° centigrade, even under high load. The location of the amalgam and containing the amalgam within the location permits efficient operation of the germicidal lamp at higher loading, and resulting higher temperatures. Additionally, by containing the amalgam in a restricted location yet open to the interior of the germicidal lamp, the amalgam may function effectively but be retained in the desired location if the amalgam melts during the high temperature occurring during high wall loads. This is particularly important in a germicidal application where the germicidal lamp is held vertically. Unless the amalgam is held in position according to the present invention, it would fall out of position upon melting and could possibly contact an electrode, greatly shortening the life of the germicidal lamp.

Additionally, different amalgams may be utilized that may melt at the internal operating temperatures therein improving operating efficiencies. The germicidal lamp of the present invention is capable of operating at external wall temperatures ranging from about 40° C. to 140° C. This temperature range is particularly advantageous in a germicidal lamp submerged in a liquid where the temperature of the liquid may vary. Accordingly, the present invention is particularly well suited and solves problems associated with germicidal lamps vertically positioned and operated under high loads.

Figure 2B:
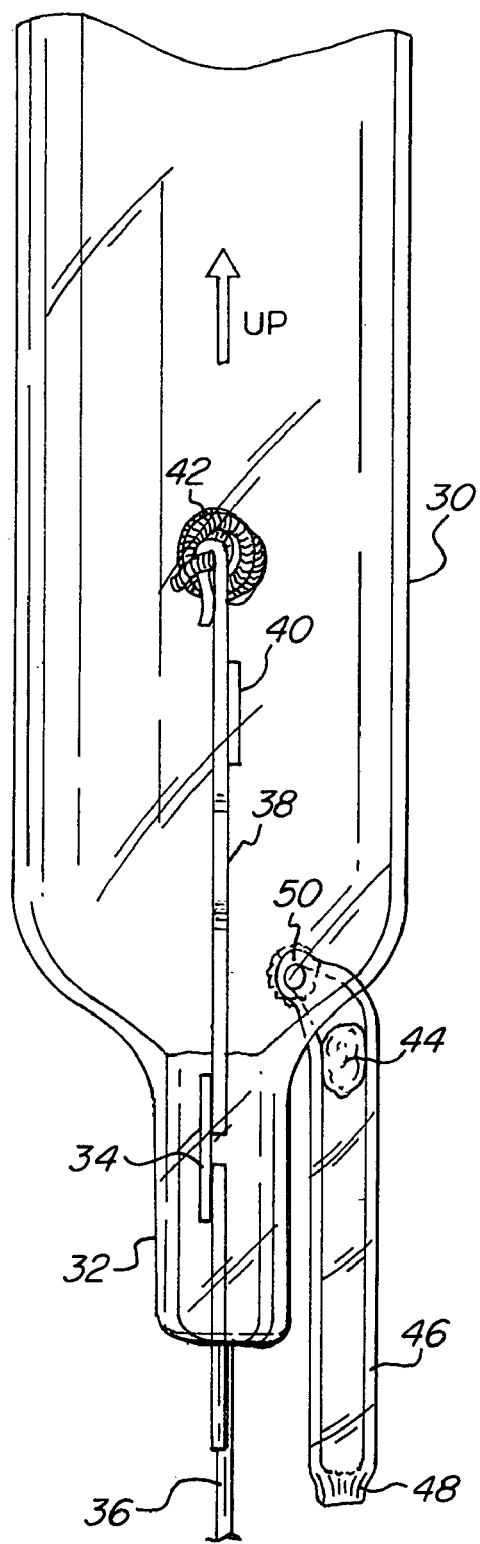
FIG. 2B illustrates the end portion of the germicidal lamp illustrated in FIG. 2A rotated 90°.
Figure 2A:
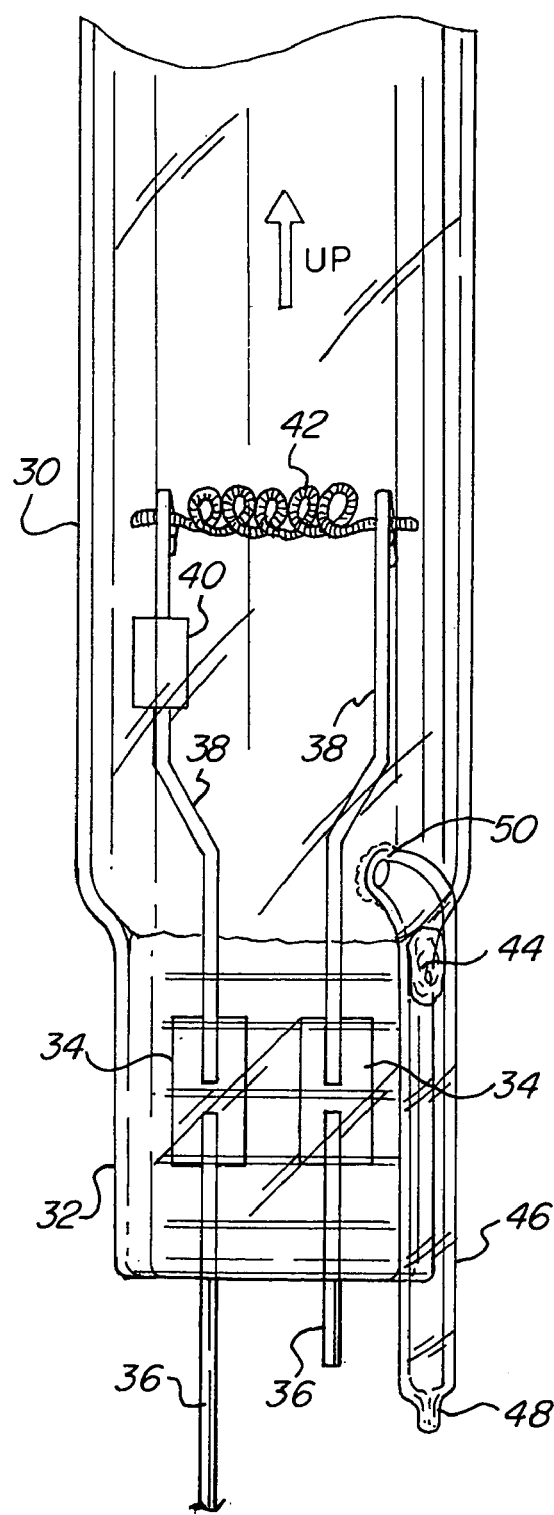
FIG. 2A is a partial view illustrating one end of a germicidal lamp according to the present invention.

FIG. 2A illustrates one end of one of the plurality of germicidal lamps 18 illustrated in FIG. 1. The opposing end of the germicidal lamp is similar. An end cap, illustrated as 22 in FIG. 1, typically would cover this end portion of the germicidal lamp. However, for purposes of illustration, the end cap has been removed to better view the structure of the end of the germicidal lamp. A tubular quartz envelope 30 has a pressed portion 32 sealing an end thereof. The pressed end 32 seals the end against ribbon conductors 34. Wires 36 are electrically coupled to the ribbon conductors 34. The wires 36 extend out of the end cap, not illustrated, and are electrically connected to pins for making an electrical connection to the lamp. The electrical connection to the germicidal lamp may be of any conventional electrical connection technique. Electrode supports 38 extend into the interior of the germicidal lamp and hold a filament electrode 42. Placed on one of the electrode supports 38 may be auxiliary amalgam 40. The auxiliary amalgam 40 preferably is composed of an amalgam with a high melting point to prevent melting during the high temperatures associated with high wall loads. However, this auxiliary amalgam 40 is generally not sufficient to maintain the desired mercury vapor pressure for efficient operation of the germicidal lamp. Additionally, this auxiliary amalgam 40 may not be required but may be utilized in some applications.

Formed on the quartz envelope 30 between the sealed end 32 and the filament electrode 42 is an amalgam container 46. The amalgam container 46 may be a quartz or glass tube communicating with the interior of the quartz envelope 30. A restricted open end 50 is formed adjacent the quartz envelope 30. Amalgam 44 is placed within the amalgam container 46. The amalgam container 46 is sealed at sealed end 48. During manufacture of the germicidal lamp, the amalgam container 46 may be used to evacuate the quartz envelope 30 as well as to introduce other substances, such as an inert gas, prior to the placement of an amalgam 44 and being sealed at sealed end 48. The restricted open end 50 is sufficiently small to prevent the amalgam 44 from passing therethrough. However, the amalgam is in communication through the restricted open end 50 to the interior of the quartz envelope 30. Therefore, the mercury vapor pressure within the quartz envelope 30 may be controlled by the absorption and release of mercury by the amalgam 44. The amalgam 44 may be any conventional amalgam well known for the purpose of controlling the mercury vapor pressure in a low pressure mercury vapor gas discharge lamp. However, because the amalgam 44 is retained in the amalgam container 46, the type of amalgam 44 selected could be an amalgam that has desirable properties, but would melt at the expected high temperatures resulting from high wall loads and improved output.

FIG. 2B illustrates another view of a portion of the end of the gas discharge lamp illustrated in FIG. 2A. In FIG. 2B, the end of the gas discharge lamp is rotated 90° from the view illustrated in FIG. 2A.

Figure 3B:
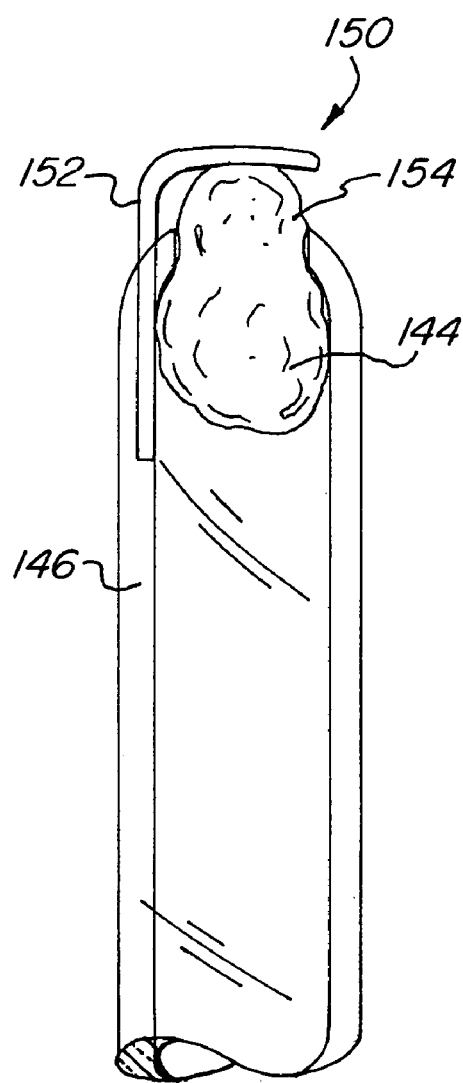
FIG. 3B is an enlarged view illustrating an amalgam container of the embodiment illustrated in FIG. 3A.
Figure 3A:
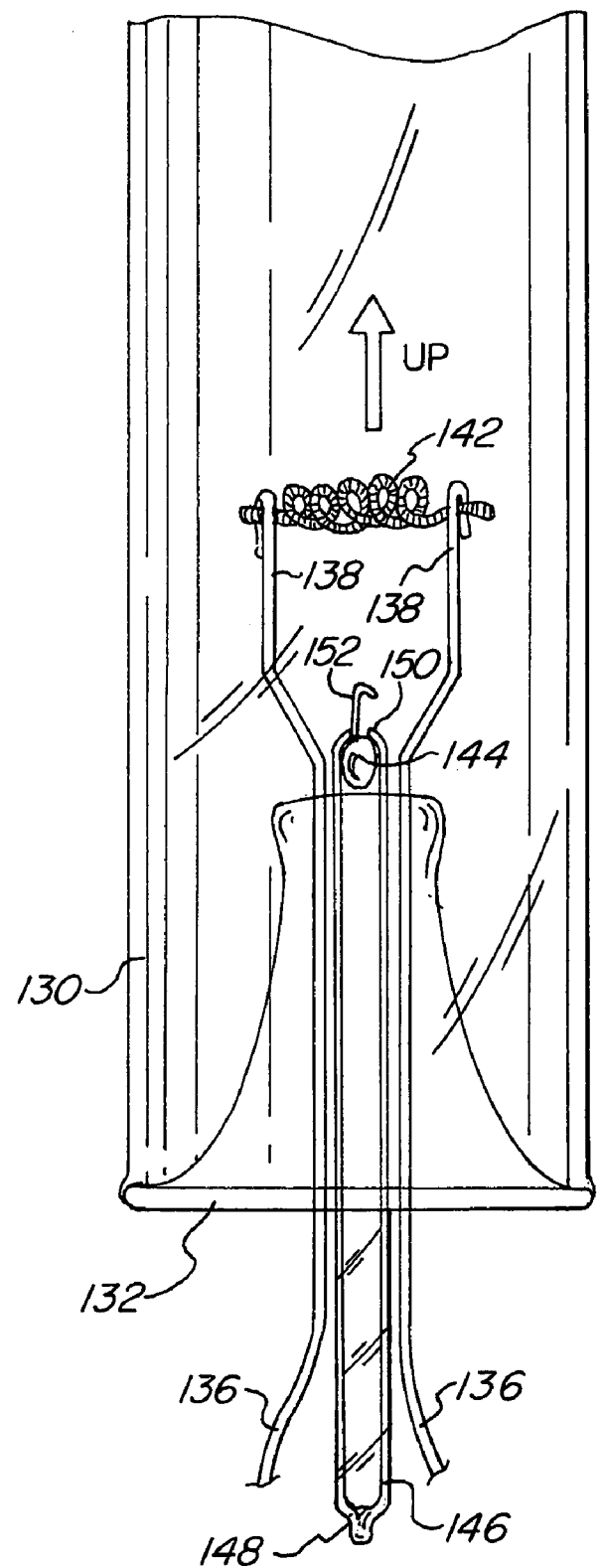
FIG. 3A is a partial view illustrating one end of a germicidal lamp according to another embodiment of the present invention.

FIGS. 3A and 3B illustrate another embodiment of an amalgam container for retaining the amalgam between the end of the lamp and the electrode. In FIG. 3A, a glass cylindrical or tubular envelope 130 has a sealing stem 132 used to seal the end of the tubular envelope 130. The sealing stem 132 has electrode supports 138 formed therein. One end of the electrode supports 138 hold a filament electrode 142 with the other end of the electrode supports 138 passing through the sealing stem 132 and are electrically coupled to wires 136. Wires 136 are electrically connected to pins, not illustrated in FIG. 3A, used to power the germicidal lamp. Formed within the sealing stem 132 is an amalgam container 146. The amalgam container 146 has a sealed end 148 and a restricted open end 150. Also formed adjacent the restricted open end 150 is a metal hook retainer 152. The combination of the restricted open end 150 and the hook retainer 152 prevents amalgam 144 from passing therethrough and into the interior of the glass tubular envelope 130. The restricted open end 150 and the hook retainer 152 are configured such that a gap formed there between is capable of retaining the amalgam even when in a fluid or liquid state. The amalgam typically being a mercury compound, generally has a property of being viscous yet capable of being retained within an opening having small enough dimensions. Accordingly, the surface of the amalgam 144 is opened to the interior of the tubular envelope 130 of the germicidal lamp, but is retained in position behind the filament electrode 142 and adjacent the end of the germicidal lamp. The amalgam container 146 may be a small tube that is also used to evacuate the interior of the germicidal lamp as well as introduce other materials, such as an inert gas, during manufacture of the germicidal lamp prior to sealing.

FIG. 3B is an enlarged view illustrating a portion of the amalgam container 146. As more clearly illustrated in FIG. 3B, the restricted open end 150 is formed by a hole 154 within the amalgam container 146 and the hook retainer 152. The hook retainer 152 may be made of a metal material that is imbedded within a side of the glass amalgam container 146. The amalgam 144 is thereby retained in position even when the germicidal lamp is held vertically during operation.

The present invention makes possible a high output mercury vapor gas discharge germicidal lamp that can be heavily loaded without overly heating an amalgam. The position of the amalgam outside of the arc path and in a cooler location behind the electrode prevents the amalgam from being overheated. Overheating of the amalgam compromises the efficient operation of the germicidal lamp. Additionally, the restriction and containing of the amalgam within the desired location makes possible operation of the germicidal lamp in a vertical position while under high load. The present invention also makes possible the efficient operation of a germicidal lamp over a relatively wide range of operating temperatures. This is particularly important when used in waste water treatment due to the range of waste water temperature. Additionally, since a higher load high output germicidal lamp is obtained with the present invention, fewer lamps are needed to achieve a desired germicidal action thereby resulting in the need for fewer lamps and resulting in lower cost. Further, maintenance costs are reduced due to the use of fewer germicidal lamps.

While the present invention has been described with respect to various embodiments, it should be appreciated by those skilled in the arts that various modifications may be made without departing from the spirit and scope of this invention.

What is claimed is:

1. A germicidal ultraviolet low pressure mercury vapor discharge lamp comprising:
   a tube having a first end and a second end;
   a first electrode placed in the first end of said tube;
   a second electrode placed in the second end of said tube, an arc path formed between said first and second electrodes, whereby when the germicidal ultraviolet low pressure mercury vapor discharge lamp is energized an arc is formed between said first and second electrodes; and
   an amalgam retained adjacent one of said first and second electrodes out of the arc path between said first and second electrodes, said amalgam retainer comprises a glass tube having a restricted opening communicating with an interior space of the germicidal ultraviolet low pressure mercury vapor discharge lamp; and
   a metal hook attached to said amalgam retainer adjacent the restricted opening covering only a portion of the restricted opening.

2. A germicidal ultraviolet low pressure mercury vapor discharge lamp comprising:
   an elongated glass tube having a first end and a second end and an interior and exterior wall surface;
   a first electrode placed in the first end of said elongated glass tube;
   a first pressed end sealing the first end of said elongated glass tube;
   a second electrode placed in the second end of said elongated glass tube, an arc path formed between said first and second electrodes, whereby when the germicidal ultraviolet low pressure mercury vapor discharge lamp is energized an arc is formed between said first and second electrodes;
   a second pressed end sealing the second end of said elongated glass tube;
   an amalgam container attached to the exterior wall surface adjacent said first pressed end of said elongated glass tube and open to the interior located between said first electrode and the first end of said elongated glass tube; and
   retainer means, formed on an end of said amalgam container adjacent the exterior wall surface, for retaining an amalgam in said amalgam container,
   whereby the germicidal ultraviolet low pressure mercury vapor discharge lamp is capable of being positioned vertically and operated at high wall loads while retaining the amalgam in the predetermined position out of the arc path.

3. A germicidal ultraviolet low pressure mercury vapor discharge lamp as in claim 2 further comprising:
   electrical pin contacts coupled to said first and second electrodes and positioned adjacent the first end.

4. A germicidal ultraviolet low pressure mercury vapor discharge lamp as in claim 2 wherein:
   said amalgam container comprises a glass tube; and
   said retainer means comprises a restricted opening communicating with the interior of the germicidal ultraviolet low pressure mercury vapor discharge lamp.

5. A germicidal ultraviolet low pressure mercury vapor discharge lamp as in claim 2 further comprising:
   a protective sleeve placed over said elongated glass tube.

6. A germicidal ultraviolet low pressure mercury vapor discharge lamp as in claim 2 wherein:
   said amalgam container and said retainer means retains an amalgam in position when the germicidal ultraviolet low pressure mercury vapor discharge lamp is operated at wall loads greater than two hundred and fifty milliwatts per centimeter squared.

7. A germicidal ultraviolet low pressure mercury vapor discharge lamp having a predetermined operating temperature for use in the treatment of waste water comprising:
   an elongated glass tube having a first end and a second end and an interior;

a first electrode placed in the first end of said elongated glass tube;

a second electrode placed in the second end of said elongated glass tube, an arc path formed between said first and second electrodes, whereby when the germicidal ultraviolet low pressure mercury vapor discharge lamp is energized an arc is formed between said first and second electrodes; and an amalgam container attached to said elongated glass tube at the first end open to the interior and located between said first electrode and the first end of said elongated grass tube;

an amalgam placed in said amalgam container, said amalgam having a melting point lower than the predetermined operating temperature of said germicidal ultraviolet low pressure mercury vapor discharge lamp; and retainer means, formed on said amalgam container, for retaining said amalgam in said amalgam container when said amalgam is melted, said amalgam container comprises a tube having an opening, said retainer means comprises a metal hook placed adjacent the opening, said metal hook covering only a portion of the opening, whereby the germicidal ultraviolet low pressure mercury vapor discharge lamp is capable of being positioned vertically and operated at high wall loads while retaining said amalgam in the predetermined position out of the arc path.

8. A germicidal ultraviolet low pressure mercury vapor discharge lamp having a predetermined operating temperature for use in the treatment of waste water as in claim 7 wherein:

the germicidal ultraviolet low pressure mercury vapor discharge lamp is operated at wall loads greater than two hundred and fifty milliwatts per centimeter squared.

9. A germicidal ultraviolet low pressure mercury vapor discharge lamp having a predetermined operating temperature for use in the treatment of waste water as in claim 7 wherein:

the germicidal ultraviolet low pressure mercury vapor discharge lamp is operated at an internal temperature between said first and second electrodes greater than one hundred and forty degrees centigrade and at the predetermined position of the amalgam less than one hundred and forty degrees centigrade.

* * * * *